United States Patent
Rockwell et al.

(10) Patent No.: US 6,381,492 B1
(45) Date of Patent: Apr. 30, 2002

(54) DEFIBRILLATOR WITH MODE CHANGING INFRARED COMMUNICATIONS

(76) Inventors: Martin G. Rockwell, 26300 SW. Graham Ferry Rd., Sherwood, OR (US) 97140; Gregory D. Brink, 1230 Clifton Ct.; Jonathan N. Andrews, 1855 NW. 8th St., both of McMinnville, OR (US) 97128; David L. Burton, 15150 NW. Orchard View Rd.; Patricia A. Arand, 2417 Pinehurst Dr., both of McMinnville, OR (US) 97128; Nancy H. Forman, 7950 SW. Green La., Beaverton, OR (US) 97008; Kenneth S. Rucker, 213 Hilltop Dr., Newberg, OR (US) 97132; John Kent, 2835 Leathers La., McMinnville, OR (US) 97132; Daniel J. Powers, 2145 Squak Mountain Loop SW., Issaquah, WA (US) 98027

( * ) Notice: Subject to any disclaimer, the term of this patent is extended or adjusted under 35 U.S.C. 154(b) by 0 days.

(21) Appl. No.: 09/545,665

(22) Filed: Apr. 7, 2000

Related U.S. Application Data

(62) Division of application No. 09/164,443, filed on Sep. 30, 1998, now Pat. No. 6,141,584.

(51) Int. Cl.[7] .................................................. A61N 1/39
(52) U.S. Cl. .................................. 607/5; 607/60; 607/30
(58) Field of Search ............................... 607/3–5, 30, 32, 607/59, 60

(56) References Cited

U.S. PATENT DOCUMENTS

| | | | |
|---|---|---|---|
| 4,150,284 A | 4/1979 | Trenkler et al. | |
| 4,151,407 A | 4/1979 | McBride et al. | |
| 4,957,348 A | 9/1990 | May | |
| 4,987,902 A | 1/1991 | Couche | |
| 5,085,224 A | 2/1992 | Galen et al. | |
| 5,224,485 A | 7/1993 | Powers et al. | |
| 5,237,663 A | 8/1993 | Srinivasan | |
| 5,343,869 A | 9/1994 | Pross et al. | |
| 5,371,692 A | 12/1994 | Draeger et al. | |
| 5,396,078 A | 3/1995 | Klaus | |
| 5,419,336 A | 5/1995 | Margison | |
| 5,446,678 A | 8/1995 | Saltzstein et al. | |
| 5,487,751 A | 1/1996 | Radons et al. | |
| 5,495,358 A | 2/1996 | Bartig et al. | |
| 5,549,659 A | 8/1996 | Johansen et al. | |
| 5,562,621 A | 10/1996 | Claude et al. | |
| 5,579,001 A | 11/1996 | Dempsey et al. | |
| 5,605,150 A | 2/1997 | Radons et al. | |
| 5,646,402 A | 7/1997 | Khovaylo et al. | |
| 5,662,690 A | * 9/1997 | Cole et al. ...................... | 607/5 |
| 5,683,423 A | 11/1997 | Post | |
| 5,687,734 A | 11/1997 | Dempsey et al. | |
| 5,782,878 A | * 7/1998 | Morgan et al. ................ | 607/5 |
| 5,957,838 A | 9/1999 | Rantala ....................... | 600/300 |
| 6,021,349 A | * 2/2000 | Arand et al. .................... | 607/5 |
| 6,148,233 A | * 11/2000 | Owen et al. ................... | 607/5 |
| 6,269,267 B1 | * 7/2001 | Bardy et al. ................... | 607/5 |

\* cited by examiner

*Primary Examiner*—Kennedy Schaetzle

(57) ABSTRACT

A defibrillator having infrared communication capability is provided. The wireless communications capability is implemented using infrared light or RF communications and standardized communications protocols such as the IrDA protocol to allow for ready communication between defibrillators such as during handoffs of patient along the Chain of Survival. The wireless communications network also allows for communications between a defibrillator and a host computer such as a palmtop for incident report generation after each handoff. Another embodiment of the present invention provides for a defibrillator having an infrared mode switch to allow for restricted access to advanced cardiac life support (ACLS) features of the defibrillator. A further embodiment of the present invention provides for a defibrillator having a remote training mode that is implemented via wireless communications. Another embodiment of the present invention provides for a defibrillator test system that is implemented via wireless communications. A further embodiment of the present invention provides for a live ECG telemetry data link using the wireless communications system.

20 Claims, 11 Drawing Sheets

DEFIBRILLATOR WITH MODE CHANGING INFRARED COMMUNICATIONS

This is a divisional of application Ser. No. 09/164,443 filed on Sep. 30, 1998, now U.S. Pat. No. 6,141,584.

BACKGROUND OF THE INVENTION

This invention relates to medical equipment and in particular to a defibrillator having wireless communications for transferring information to and from the defibrillator in a wireless network.

One frequent consequence of heart disease is the development of cardiac arrest associated with a heart arrhythrmia such as ventricular fibrillation. Ventricular fibrillation may be treated by delivering an electrical shock to the patient's heart through the use of a defibrillator. Cardiopulmonary resuscitation (CPR) is commonly used to maintain life support for victims of cardiac arrest until a defibrillator can be deployed to treat the arrhythmia.

The chances of surviving a cardiac arrest decrease rapidly over the time following the arrest. Quick response to a cardiac arrest by performing CPR and by administering a defibrillating shock is therefore of critical importance. The American Heart Association's "Chain of Survival" recites the following steps:

1. Early access to emergency care, such as by activating an emergency medical system (EMS);
2. Early CPR initiated by a bystander or other first responder using basic life support (BLS) techniques to help the patient survive until more advanced care arrives;
3. Early defibrillation; and
4. Early advanced cardiac care. The benefits of this approach are discussed in more detail in Cummins, et al. "Improving Survival From Sudden Cardiac Arrest: the 'Chain of Survival' Concept," 83 Circulation 1832–47 (May 1991).

EMS providers are playing an active role in implementing the Chain of Survival concept. Tiered EMS systems are emerging in many geographical areas and are typically divided between first responders, BLS (basic life support) providers, and ACLS (advanced cardiac life support) providers. First responders and BLS providers, often called EMT(B) or EMT-basic, the front line personnel who are first to reach a patient, are now being trained and authorized to use automatic external defibrillators (AEDs) to provide early defibrillation.

AEDs deliver a high-amplitude current impulse to the heart in order to restore normal rhythm and contractile function in the patients who are experiencing ventricular fibrillation (VF) or ventricular tachycardia (VT) that is not accompanied by a palpable pulse. AEDs differ from manual defibrillators in that AEDs can automatically analyze the electrocardiogram (ECG) rhythm to determine if defibrillation is necessary. In nearly all AED designs, the first responder is prompted to press a shock button to deliver the defibrillation shock to the patient. Paramedic defibrillators often combine the AED and manual functions into one unit to allow for use by personnel with differing levels of training.

AEDs are designed to be used primarily by first responders who may not be trained in ACLS techniques. In the pre-hospital setting, these first responders may include emergency medical technicians trained in defibrillation (EMT-Ds), police officers, flight attendants, security personnel, occupational health nurses, and firefighters. AEDs can also be used in areas of the hospital where personnel trained in ACLS are not readily available. In such cases, it may be desirable to provide a defibrillator which operates in an AED mode but with manual functions such as cardiac monitoring disabled.

In more recent AED designs such as the Heartstream Forerunner® defibrillator, the AED functions have been logically grouped into step 1, "power on"; step 2, "analyze"; and step 3, "shock." More sophisticated audio prompts have been added in addition to the visual prompts provided by the LCD display. The transition from step 1 to step 2 may be initiated by the defibrillator, such as upon detection of patient contact between the defibrillation electrodes to begin the ECG analysis as soon as possible. Proceeding from step 2 to step 3 according to the AED personality requires the user to press a shock button upon recognition of a shockable rhythm by the ECG analysis. In this way, the AED personality is commonly understood to mean semi-automatic rather than fully automatic defibrillation.

In many EMS systems, the next link in the Chain of Survival is provided with the arrival of ACLS trained paramedics equipped with full featured defibrillators/cardiac monitors ("paramedic defibrillators"). Alternatively, if no ACLS trained personnel are available, the patient is directly transported to a hospital emergency department where ACLS care can be provided. In either case, a handoff of the patient takes place between the first responder and subsequent ACLS personnel.

As part of the handoff process, medical information obtained at the scene and stored within the defibrillator must be transferred along with the patient regarding what has taken place during treatment. Commonly referred to as a code summary or an event summary, such information typically may include an ECG strip as well as markers for such events as the time of initial cardiac arrest, initiation of CPR, administration of drugs, delivery of defibrillation shocks, and so on. In addition, an audio recording ("voice strip") that documents the verbal remarks of the first responders is often provided. Such medical information contained in the event summary should be as complete and accurate as possible to ensure continuity of care and to enable the attending physician to provide the most appropriate follow-up care to the patient. It is desirable that the medical information stored in the event summary have the ability travel alongside the patient during the various handoffs along the Chain of Survival.

The event summary may also be used by the first responder to aid in the generation of incident reports. Such incident reports often must be filed according to the requirements of the local EMS system, both for quality control and documentation. The event summary may be down-loaded or transferred to a host computer running data management software that provides for displaying, analyzing, and playing back the medical information from the event summary in a meaningful manner to reconstruct the events that took place during the emergency treatment of the patient.

Prior art defibrillators provided documentation using hard copy devices such as built-in printers to produce the ECG strip. Event markers, such as the time each defibrillation shock is administered, could be marked on the edge of the paper ECG strip. An audio recording was typically provided using a built-in audio cassette recorder. Because the ECG strip was not stored but simply printed on a paper tape, retaining a copy of the ECG strip solely for report generation was impractical.

More recent AED designs such as the Heartstream Forerunner® defibrillator record the event summary information digitally on a removable storage medium in the form of a PCMCIA memory card. A method for gathering event data is discussed in U.S. Pat. No. 5,549,115, "Method and Apparatus for Gathering Event Data Using A Removable Data Storage Medium and Clock", issued Aug. 27, 1996, to Morgan et al., and assigned to Heartstream, Inc. The information contained on the PCMCIA card is transferred by physically removing the PCMCIA card from the defibrillator and plugging it into another device such as a card reader connected to a host computer which up-loads the information to the data management software. Other AED designs provide for transferring the information via a wired connection such as an RS-232 serial link to the host computer.

Manually transferring memory cards along with the patient during a handoff from the first responder to an ACLS provider is not practical for a number of reasons. Memory cards are easily lost and may not be compatible with the defibrillator belonging to the ACLS personnel. After the handoff, the event summary stored on the memory card is then unavailable for the first responder to generate incident reports since the memory card has since been transported with patient.

Various methods for transmitting ECG information gathered remotely via telemetry back to an ECG monitor are discussed in U.S. Pat. No. 5,549,659, "Communication Interface for Transmitting and Receiving Serial Data Between Medical Instruments", U.S. Pat. No. 5,224,485, "portable Data Acquisition Unit", and U.S. Pat. No. 5,085,224, "Portable Signaling Unit For An EKG." These methods teach sending ECG information via either hardwired or radio telemetry links for cardiac monitoring and diagnostic applications.

A method for optically coupling an ECG signal from the electrode leads to the ECG circuit is discussed in U.S. Pat. No. 4.987,902, "Apparatus for Transmitting Patient Physiological Signals" to Charles A. Couche. The opto-coupler taught by Couche provides voltage isolation between an isolated circuit such as an ECG front end and a non-isolated circuit within the medical instrument. A complex coding arrangement transforms the ECG signal into a series of pulses to avoid the use of analog to digital converters ahead of the opto-coupler in the ECG front end. However, there is no teaching by Couche to couple the ECG signal to other medical instruments or defibrillators.

ACLS personnel typically use paramedic defibrillators that contain more advanced cardiac monitoring and analysis functions such as 12 lead ECG, along with other functions such as cardiac pacing. Paramedic defibrillators generate their own event summary similar to that of AEDs and presently suffer from many of the same shortcomings as AEDs in terms of transferring medical information to and from other devices. The ECG strips that are generated by many prior art manual defibrillators are in the form of paper strips produced by a built-in printer, sometimes with annotations in the margin to mark various events during the treatment of the patient. During a handoff from ACLS personnel to the hospital emergency department, the event summary contained on the paper ECG strip is sent along with the patient, typically with no event summary information from the prior handoff from the first responder.

In an effort to reduce the number and types of defibrillators in an EMS system, it may be desirable to standardize on one type of defibrillator that may be used by both BLS and ACLS personnel. Because the training level and qualifications of BLS and ACLS personnel are different, the functions available on the defibrillator must necessarily be different. The functions may be grouped into AED functions and ACLS functions. In most cases, the AED functions are simply a subset of the ACLS functions. It is desirable that access to the ACLS functions be restricted to qualified ACLS personnel but in a way that is not overly difficult to administer by EMS personnel.

Access control to ACLS functions was accomplished in prior art defibrillators with mechanical key switches or programmable passwords entered via front panel buttons. Mechanical key switches are problematic because the key is easily lost, rendering the ACLS functions unavailable. On the other hand, the key may simply be left in the key switch for ready access in an emergency, effectively bypassing the safeguard. Similarly, passwords controlling access to ACLS functions may simply be written on the front panel of the defibrillator so that they would not have to be memorized. Thus, limiting access to the ACLS functions was difficult to administrate and quickly bypassed by personnel in the field for practical reasons.

In many EMS jurisdictions, the attending physician must be able to see the live ECG strip in real time while the patient is still in the field in order to issue orders to the EMTs to defibrillate, to administer drugs or start intravenous fluids. Such ECG strips have been typically transmitted via dedicated radio telemetry channels or cellular modems to the hospital emergency department. The defibrillator can be configured to operate as a cardiac monitor with its ECG output provided to the radio link. U.S. Pat. No. 5,593,426 "Defibrillator System Using Multiple External Defibrillators and a Communications Network", issued Jan. 14, 1997 to Morgan et al. and assigned to Heartstream, Inc. describes a communication network between multiple defibrillators and a communication station. Each defibrillator may be coupled via an infrared link to a defibrillator communicator that forms part of the communication network. However, there is no teaching by Morgan et al. of wireless communication between defibrillators.

Obtaining a live ECG strip is more often obtained by connecting an "ECG out" port on the defibrillator to either analog or digital radio telemetry channels which transmit the ECG to the attending physician. Such a communications link is very specialized, is custom tailored to work for specific equipment, and requires a connection using a data communications cable ("patch cable") to other communications equipment within the ambulance.

Defibrillators, like most types of sophisticated electronic equipment, now contain at least one microprocessor or embedded controller to perform its basic functions. Such microprocessors execute software programs stored as firmware in non-volatile memory such as read-only memory (ROM). Upgrading and maintaining the firmware is an important aspect in the manufacturing, service, and support of the defibrillator throughout its useful life. Such support typically involves the invasive activity of opening the housing of the defibrillator to physically change ROMs. In some cases, firmware upgrades could be performed with a software download from a maintenance computer via a serial port. Such activities are difficult enough to require the defibrillator be taken out of service and sent in to a central repair depot or service shop that substantially increases the overall life cycle cost of the defibrillator for the customer.

The inability to easily transfer medical information alongside the patient through the Chain of Survival has therefore been a long felt need not presently addressed by the prior art. The further inability to easily transfer information between a defibrillator and host computers for providing defibrillator service and maintenance, enabling or disabling access to ACLS functions, and training of defibrillator operators have also been long felt needs not presently addressed by the prior art. Therefore, it would be desirable to provide a wireless communication network for defibrillators using infrared data communications that allows for ready transfer of information to and from the defibrillator.

SUMMARY OF THE INVENTION

In accordance with the present invention, a defibrillator having wireless communication capability is provided. A first embodiment of the present invention provides for wireless communication network for defibrillators. The wireless communications capability may be implemented using infrared light and a standardized communications protocols such as according to the IrDA protocol to allow for ready communication between defibrillators such as during handoffs of patient along the Chain of Survival. Alternatively, the wireless communications capability may be implemented using radio frequency (RF) communications. The wireless communications network also allows for communications between a defibrillator and a host computer such as a palmtop or laptop computer for incident report generation.

Another embodiment of the present invention provides for a defibrillator having an infrared mode switch to allow for restricted access to ACLS functions of the defibrillator.

Another embodiment of the present invention provides for a defibrillator having a remote training mode that is implemented via wireless communications. A training system including a training simulator and computer containing training scenarios communicates via the defibrillator via the wireless communications network to allow for the training of personnel without specialized hardware or communications requirements.

Another embodiment of the present invention provides for a defibrillator maintenance system that is implemented via wireless communications. A defibrillator maintenance system including a patient simulator and a computer containing defibrillator software communicates with the defibrillator via the wireless communication network to allow for defibrillator testing and non-invasive firmware upgrades.

Another embodiment of the present invention provides for a live ECG telemetry data link using the wireless communications system. The defibrillator provides live ECG telemetry via the wireless communication network to a telemetry transceiver or cellular modem that communicates via radio link to another telemetry transceiver. The live ECG telemetry is then provided to a computer for display in a number of ways such as via a web browser or assembled as a bit map image such as a facsimile page.

One feature of the present invention is to provide a defibrillator with infrared communications capability.

Another feature of the present invention is to provide a wireless communications network for defibrillators.

A further feature of the present invention is to provide a method of communicating information between medical equipment through a series of handoffs.

An additional feature of the present invention is a method of uploading medical information to a local computer via an infrared link.

Other features, attainments, and advantages will become apparent to those skilled in the art upon a reading of the following description when taken in conjunction with the accompanying drawings.

DETAILED DESCRIPTION OF THE INVENTION

Figure 1:
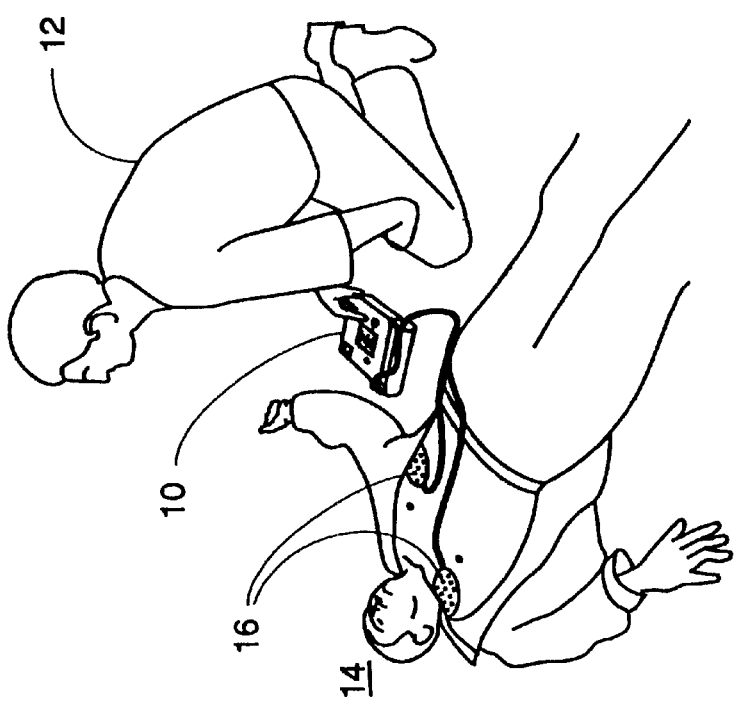
FIG. 1 is an illustration of a defibrillator being applied to a patient suffering from cardiac arrest.

FIG. 1 is an illustration of a defibrillator 10 being applied by a first responder 12 to resuscitate a patient 14 suffering from cardiac arrest. In cardiac arrest, otherwise known as sudden cardiac arrest, the patient is stricken with a life threatening interruption to their normal heart rhythm, typically in the form of ventricular fibrillation (VF) or ventricular tachycardia (VT) that is not accompanied by a palpable pulse (shockable VT). In VF, the normal rhythmic ventricular contractions are replaced by rapid, irregular twitching that results in ineffective and severely reduced pumping by the heart. If normal rhythm is not restored quickly, a time frame commonly understood to be approximately 8 to 10 minutes, the patient 14 will die. Conversely, the quicker defibrillation can be applied after the onset of VF, the better the chances that the patient 14 will survive the event. Activating the EMS, typically with a telephone call to a local emergency telephone number such as 911 in North America, typically begins the process to obtain emergency treatment.

A pair of electrodes 16 are applied across the chest of the patient 14 by the first responder 12 in order to acquire an ECG signal from the patient's heart. The defibrillator 10, if configured as an AED, then automatically analyzes the ECG signal to detect ventricular fibrillation (VF). If VF is detected, the defibrillator 10 signals the first responder 12 that a shock is advised. Alternatively, if the defibrillator 10 may be a paramedic defibrillator which allows the ECG waveform to be analyzed manually. After detecting VF or other shockable rhythm, the first responder 12 then presses a button on the defibrillator 10 to deliver the shock to resuscitate the patient 14.

The information surrounding the event of resuscitation is critically important to providing proper emergency care of the patient 14 further along the Chain of Survival. As the patient 14 is handed off to ACLS providers or paramedics who provide more advanced treatment and again as the patient 14 is handed off to the hospital emergency department, critical medical information embodied as a event summary, explained in more detail below, must travel with the patient 14.

Figure 2:
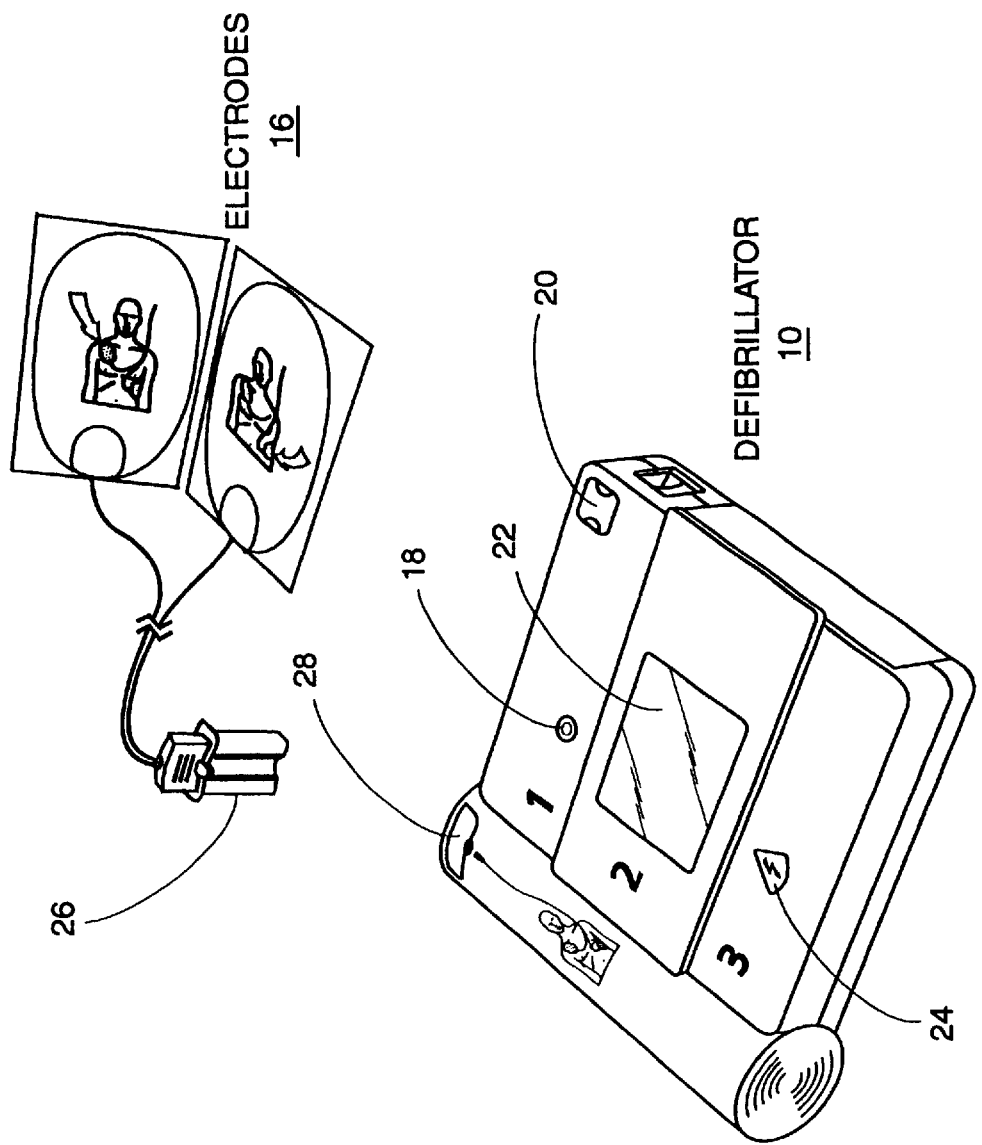
FIG. 2 is a more detailed illustration of the defibrillator and electrodes shown in FIG. 1.

FIG. 2 is a more detailed illustration of the defibrillator 10 and the pair of electrodes 16 which is shown for purposes of example and not limitation as an AED. Configured as an AED, the defibrillator 10 is optimized for small physical size, light weight, and relatively simple user interface capable of being operated by personnel without high training levels or who otherwise would use the defibrillator 10 only infrequently. A paramedic or clinical defibrillator, on the other hand, tends to be larger, heavier, and have a more complex user interface capable of supporting a larger number of manual monitoring and analysis functions. For purposes of the discussion that follows, the AED and the paramedic defibrillator may be considered two separate variations of the defibrillator 10, with the AED to be used by the first responder 12 and the paramedic defibrillator to be used by the ACLS provider.

The pair of electrodes 16 is connected to a connector 26 for insertion into a socket 28 on the defibrillator 10. On a top surface of the defibrillator 10 is located an on-off switch 18 which activates the defibrillator 10 and begins the process of the prompting the first responder 12 to connect the electrodes 16 to the patient 14. A battery condition indicator 20 provides a continual visual indication of the defibrillator status and the available battery charge. A display 22 preferably provides for display of text such as user prompts and graphics such as ECG waveforms. A shock button 24 provides for delivery of the shock to the patient 14 if a shockable rhythm is detected. The AED personality of the defibrillator 10 thus provides for a three step defibrillation process of connecting the electrodes 16 to the patient 14, analyzing the ECG signal, and administering defibrillation shocks to the patient 14 as needed for resuscitation. The third step of administering defibrillation shocks is nearly always done by prompting the user to manually press the shock button 24. Thus, AEDs generally are semi-automatic in operation rather than fully automatic.

The defibrillator 10 can be used as a paramedic defibrillator by adding more advanced manual functions, such as increasing the number of ECG leads from two to three or five leads, adding cardiac pacing and pulse oximetry functions, and so on. Adding such functions necessarily complicates the user interface of the defibrillator 10 and fundamentally changes its operation into that of a manual defibrillator. To segment the added complexity over the basic AED personality and maintain the ease of operation for the first responder 12 who needs only the AED personality, the advanced functions may be provided as an ACLS or manual personality. Access to the ACLS personality is preferably limited to ACLS providers.

Figure 3:
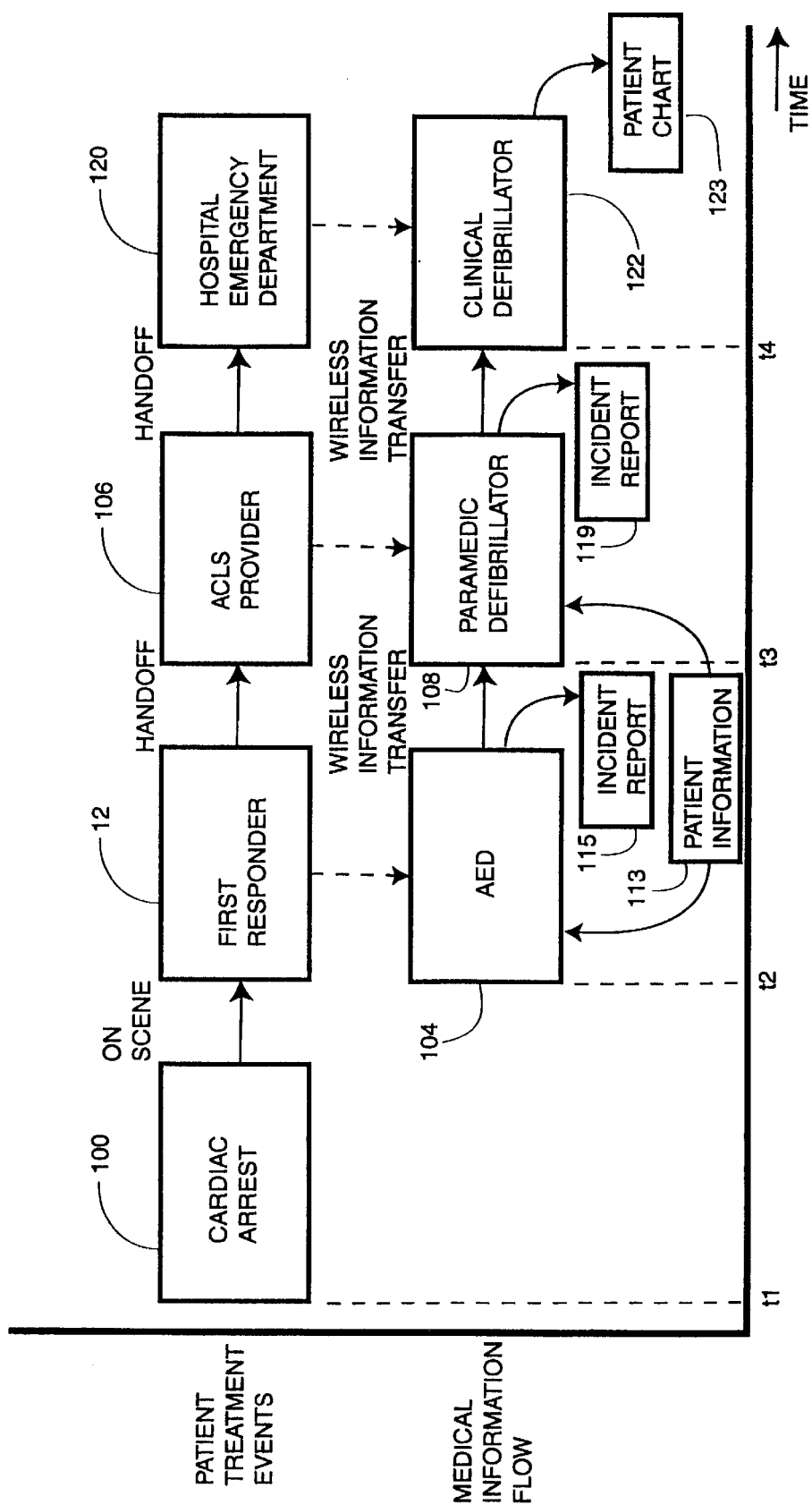
FIG. 3 is a process flow diagram illustrating the transfer of information in a wireless network among the various defibrillators during handoffs of the patient along the Chain of Survival according to the present invention.

FIG. 3 is a process flow diagram showing a sequence of patient treatment events along a horizontal time axis as may occur during a life threatening event such as cardiac arrest. Also shown is a sequence illustrating the flow of medical information containing event summaries and patient information that are passed along with the patient 14 during a series of handoffs using wireless communications according to the present invention.

In Cardiac Arrest 100, the patient 14 is stricken with cardiac arrest at time t1. The EMS is activated and early CPR (not shown) may be performed on the patient 14 to improve their chances of survival while waiting for defibrillation.

The first responder 12 arrives on the scene at time t2 in response to the cardiac arrest 100. Because the time to arrive on scene following the cardiac arrest at time t1 is critical to the survival of the patient 14, a first responder capable of providing early defibrillation such as a fire fighter or police officer located nearby equipped with an AED can respond to the emergency call.

The first responder 12 deploys an AED 104 by attaching electrodes to the patient's chest, activating the AED 104 to analyze the patient's heart rhythm in the form of an ECG signal, and then applying the defibrillation shock if recommended by the AED 104. The AED 104 begins recording an event summary after being turned on so that the events surrounding the delivery of the defibrillation shock can be recorded. The contents of the event summary are explained in more detail below. The event summary may be stored digitally in memory in the AED 104, typically in a memory card that can be removed from the AED 104 and kept for documentation and report generation purposes.

An ACLS provider 106, such as a paramedic or other personnel with the capability to provide ACLS level care, arrive on the scene at time t3 and take over the care of the patient 14 from the first responder 12. The AED 104, with the electrodes 16 still attached to the patient 14, will likely be removed in favor of a paramedic defibrillator 108 with more advanced monitoring and cardiac pacing capability during a handoff from the first responder 12 to the ACLS provider 106. Using the wireless communication according to the present invention, the AED 104 belonging to the first responder 12 then transmits its event summary to the paramedic defibrillator 108 as a wireless information transfer during the handoff process at time t3 with no physical interchange of memory cards or connection of communications cables between the AED 104 and the paramedic defibrillator 108.

Figure 5:
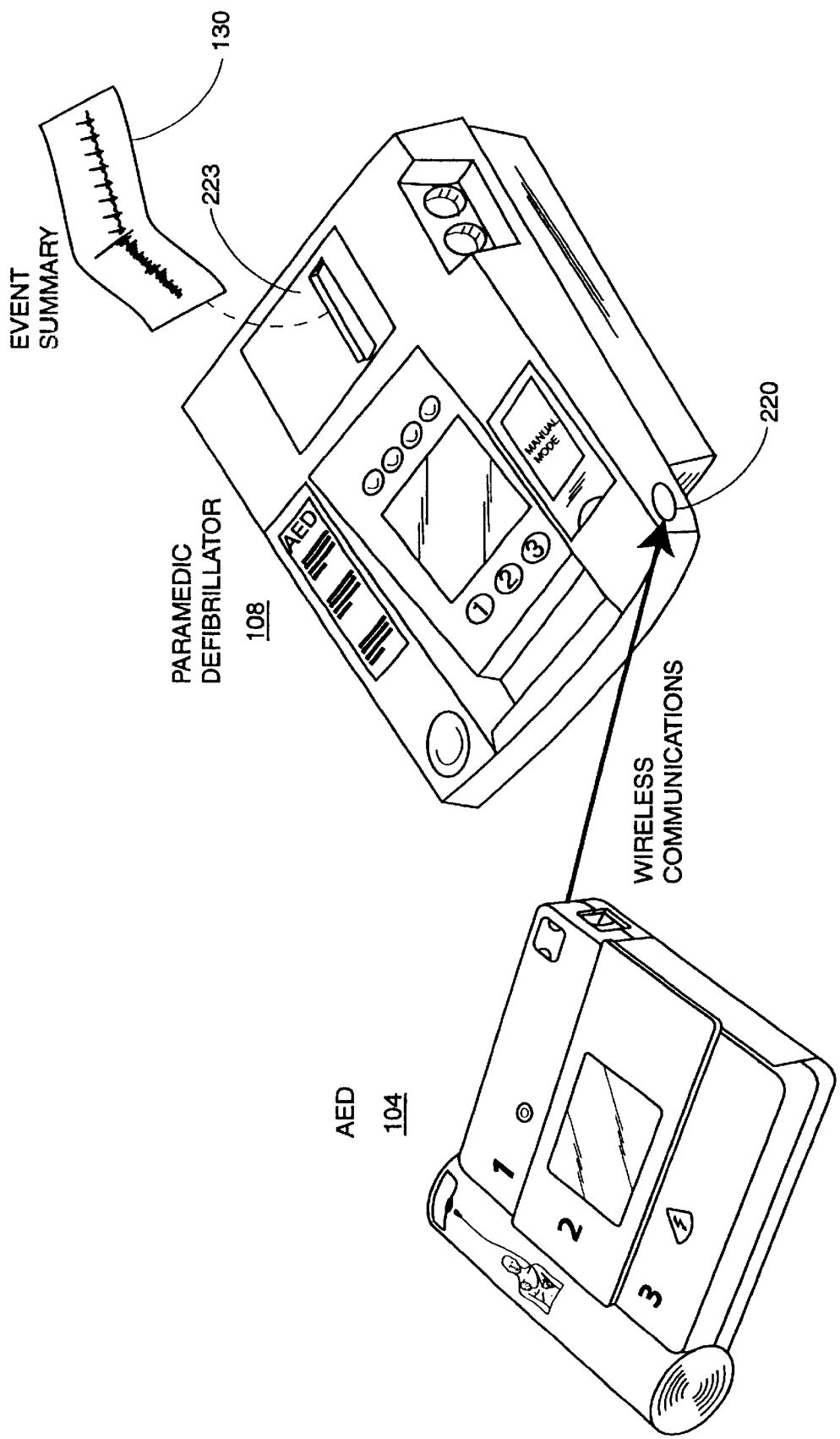
FIG. 5 is an illustration (not to scale) of the wireless information transfer of the event summary between an AED and a paramedic defibrillator according to the present invention.

In order to better enable the ACLS provider 106 to care for the patient 14 upon arriving at the scene at time t3, an event summary 130 uploaded from the AED 104 may be printed out using the printer commonly found in the paramedic defibrillator 108 as shown in FIG. 5.

FIG. 5 is an illustration of the wireless information transfer of the event summary 130 between the AED 104 and paramedic defibrillator 108 as may be done in the handoff of the patient 14 from the first responder 12 to the ACLS provider 106 (shown in FIG. 3). Infrared communications 220 on the paramedic defibrillator 108, typically seen as an optical window on the housing of the paramedic defibrillator 108, receives the event summary 130 from the AED 104. The ACLS provider 106 can then immediately obtain a print out of the event summary 130 using a printer 223 that is built into the paramedic defibrillator 108.

In this way, medical information collected by the AED 104 that is important to the immediate treatment of the patient 14 may be put to use by the ACLS provider 106. Alternatively, the event summary 130 may be downloaded to a portable printer (not shown) via wireless communications directly at the scene at time t3 to accomplish the same result, albeit with an extra printer that must be immediately available.

Referring back to FIG. 3, with the patient 14 now transported to the hospital emergency department by the ACLS provider 106, another handoff takes place at time t4 from the ACLS provider 106 to a hospital emergency department 120. The hospital emergency department 120 has its own clinical defibrillator 122. There may be no practical difference in capabilities between the paramedic defibrillator 108 and the clinical defibrillator 122.

Handing off from the paramedic defibrillator 108 to the clinical defibrillator 122 may simply be done for reasons of departmental ownership since the paramedic defibrillator 108 must be quickly returned to service in the field while the clinical defibrillator 122 remains with the hospital emergency department 120. Alternatively, the clinical defibrillator 122 may be part of a more sophisticated patient cardiac monitoring system in the hospital such as those found in an intensive care unit. Thus, a second wireless information transfer takes place from the paramedic defibrillator 108 to the clinical defibrillator 122 during the handoff from the ACLS provider 106 to the hospital emergency department 120 at time t4. The information handed off preferably contains the code summaries both from the AED 104 and the paramedic defibrillator 108.

As each of the handoffs at times t3 and t4 are completed, the event summaries collected by the AED 104 and paramedic defibrillator 108 that document what has happened to the patient 14 may be needed to generate incident reports 115 and 119 by the first responder 102 and the ACLS provider 106. The event summaries may also be used to generate a patient chart 123 for use by the hospital emergency department 120. The incident reports 115 and 119 and patient chart 123 take the event summary 130 and patient information 113 contained in the medical information to produce a report in a format needed for documentation and quality control purposes. Using the wireless communication network according the present invention, the event summary 130 may be down-loaded to a host computer back at the station or to a palm top computer, mobile computer, or peripheral such as a portable printer while still in the field. The first responder 12, for example, may press a button on the AED 104 to down-load the event summary to the host computer operating data management software which allows for review of the ECG strip, along with playback of the audio strip. The event summary can be incorporated in automated report generation software in the computer to generate the incident report 115. An incident report 119 for the ACLS provider 106 may be obtained in a similar manner.

patient information 113 may be uploaded to the AED 104 or paramedic defibrillator 108 via wireless communications from a laptop or palmtop computer in the field so that the information may accompany the patient 14 through the Chain of Survival alongside the event summary 130. In this way, the medical information including the event summary 130 and patient information 113 stays with the patient 14 in the various defibrillators that travel alongside the patient 14 through the series of handoffs. The contents of the patient information 113 are described in more detail below.

Figure 4:
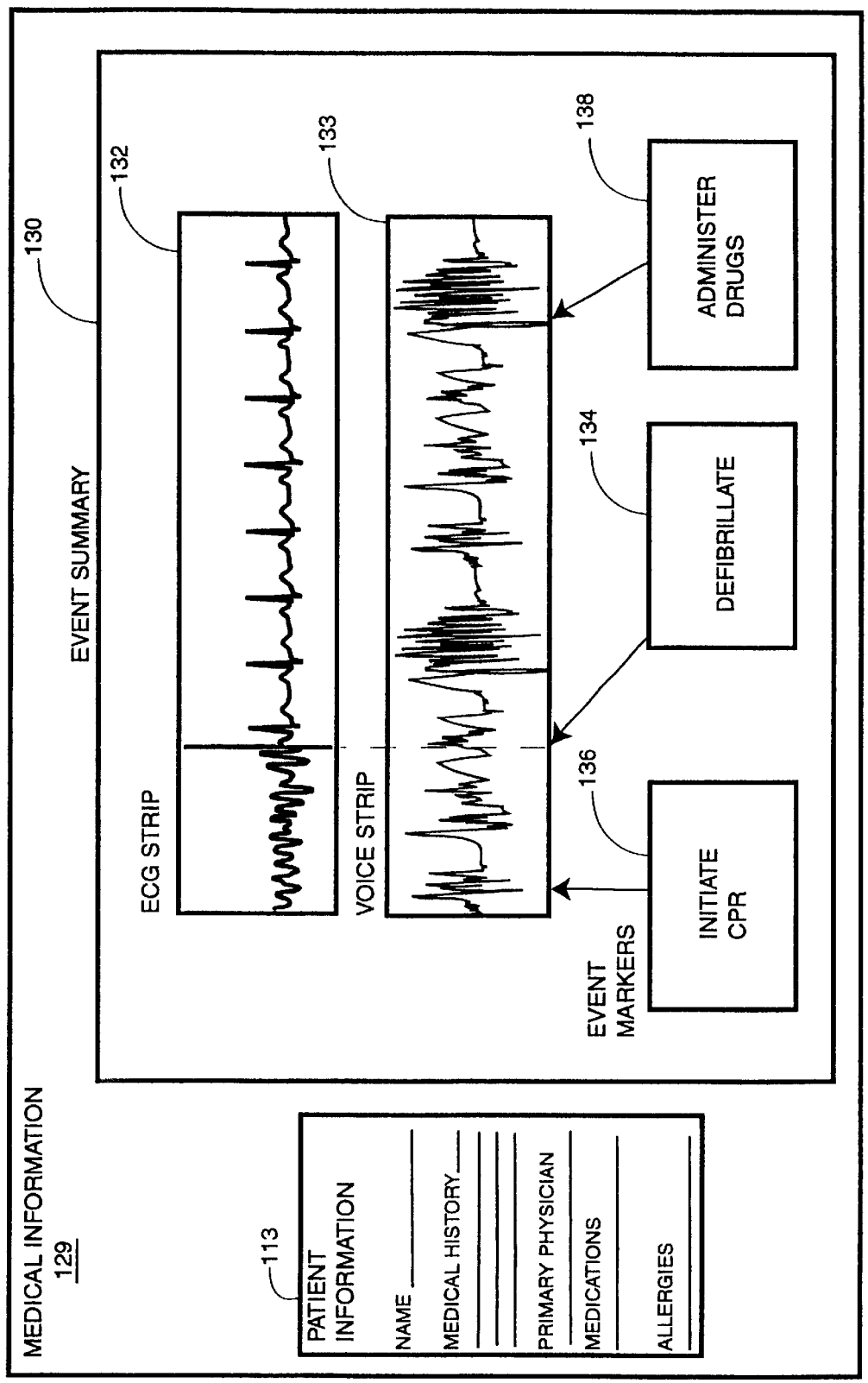
FIG. 4 illustrates the contents of an event summary and patient information generated by the defibrillator.

FIG. 4 illustrates the typical contents of medical information 129 which includes the event summary 130 and may also include the patient information 113. An ECG strip 132 is a collection of digital samples taken from the analog ECG signal. The digital samples can be reconstructed and displayed as vertical amplitude information ordered along a horizontal time axis to resemble the traditional paper ECG strip that is familiar to the physician. The digital samples of the ECG signal must therefore be stored with both amplitude and time information in memory in the defibrillator 10. Because the defibrillator 10, either in the form of the AED 104 or the paramedic defibrillator 108, may be turned on and off multiple times during a single incident, various fragments of the ECG strips 132 over different times may be contained in the event summary 130. Displaying and interpreting the fragments of the ECG strips 132 in a meaningful manner may require increased sophistication in the data management software running in the host computer.

In a similar manner to the ECG strip 132, a voice strip 133 containing audio received from a microphone located in the defibrillator 10 may be collected as a series of digital samples that can be re-assembled for audio playback by the host computer. The timing of the ECG strip 132 and the voice strip 133 are preferably correlated with each other during the playback process in the host computer in order to accurately reconstruct the events that took place during the emergency treatment of the patient 14.

Also contained within the event summary 130 are event markers 134, 136, and 138. The event markers 134, 136, and 138 are used to mark the times of various events that take place during the treatment of the patient. For example, event marker 134 labeled "Defibrillate" indicates the time at which a defibrillation shock was delivered to the patient 14. Additional information such as the energy level of the defibrillation shock may also be included with the event marker 134. Such information could either be included responsive to a key press on the defibrillator 10 for the selected event such as to mark drug delivery or automatically generated with annotations according to a predetermined event such as pressing the shock button 24. The event markers 134, 136, and 138 could each include their own dedicated voice strip that serves to mark the nature of the event. In a similar manner, the event markers 136 and 138 are used to note other events such as initiation of CPR and the administration of drugs. As many event markers as needed can be added to the event summary 130 to capture meaningful events and their respective times during the treatment of the patient 14.

The patient information 113 is likely to be a text file which information collected at the scene by the first responder 12 or ACLS provider 106. The patient information 113 may be uploaded from a laptop, palmtop, or pen-based computer (not shown) via wireless communications to either of the AED 104 or paramedic defibrillator 128 to form a portion of the medical information 129. Additions to the medical information may be made at any point along the process of treating the patient. In the hospital emergency department 120, the patient information may be downloaded along with the event summary 130 to form the patient chart 123.

Figure 6:
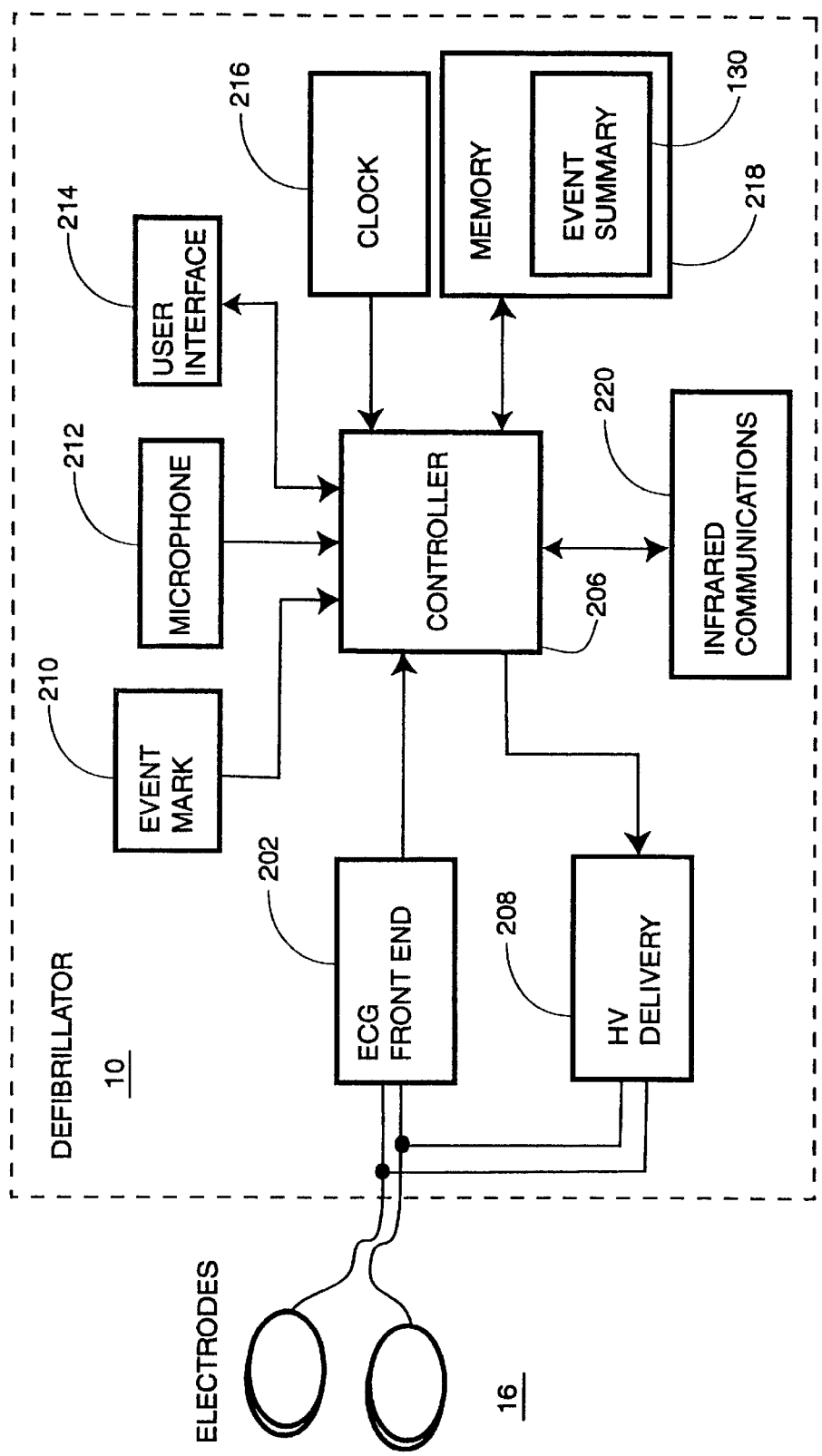
FIG. 6 is a simplified block of the defibrillator employing infrared communications to implement the wireless network of FIG. 2.

FIG. 6 is a simplified block diagram of the defibrillator 10 according to the present invention that could include the AED 104, paramedic defibrillator 108 or clinical defibrillator 122. An ECG front end 202 is connected to the pair of electrodes 16 that are connected across the chest of the patient 14. The ECG front end 202 operates to amplify, buffer, filter and digitize an electrical ECG signal generated by the patient's heart to produce a stream of digitized ECG samples. The digitized ECG samples are provided to a controller 206 that performs an analysis to detect VF, shockable VT or other shockable rhythm. If a shockable rhythm is detected, the controller 206 sends a signal to HV delivery 208 to charge up in preparation for delivering a shock. Pressing the shock button 24 (shown in FIG. 2) then delivers a defibrillation shock from the HV delivery 208 to the patient 14 through the electrodes 16.

The controller 206 is coupled to receive inputs from an event mark 210 which may be a button on the front panel that is pressed to mark an event as described above. An event may be marked according to the time of event and type of event. The event mark 210 may also be automatically generated according to predefined events, such as the pressing of the shock button 24 to record the time and energy level of the defibrillation shock. The controller 206 is coupled to further receive input from a microphone 212 to produce the voice strip 34. The analog audio signal from the microphone 212 is preferably digitized to produce a stream of digitized audio samples which may be stored as part of the event summary 130 in a memory 218.

A user interface 214 may consist of the display 22, an audio speaker and the printer 223 (not shown), and front panel buttons such as the on-off button 18 and shock button 24 for providing user control as well as visual and audible prompts. A clock 216 provides real-time clock data to the controller 106 for time-stamping information contained in the event summary 130. The memory 218, implemented either as on-board RAM, a removable memory card, or a combination of different memory technologies, operates to store the event summary 130 digitally in the memory 218 as it is compiled over the treatment of the patient 14. The event summary may include the streams of digitized ECG and audio samples which are stored as the ECG strip 132 and the voice strip 133 respectively.

To implement wireless communication, infrared communications 220 operates to communicate bi-directionally with the controller 206 to allow for up-loading and down-loading the event summary 130 as well as other information to the defibrillator 10 as explained in more detail below. The infrared communications 220 may be implemented using off-the-shelf infrared communications components and preferably using a standardized communications protocol such as according to the Infrared Data Association (IrDA). IrDA is an industry-based group of over 150 companies that have developed communication standards especially suited for low cost, short range, cross-platform point-to-point communications at a wide range of speeds using infrared technology. These wireless communications standards have been adapted particularly well in mobile computing environments such as laptops and palmtops as well as peripherals such as printers to allow for ready transfer of information.

RF communications (not shown) may be readily substituted for the infrared communications 220 to operate in a substantially similar manner in order to implement wireless communications. The RF communications may be readily implemented using commercially available, off the shelf components that employ standardized communications protocols at the network and link levels. For example, wireless transceivers that operate in the 900 MHz radio band and employ a TCP/IP network communications protocol to implement a wireless Ethernet local area network (LAN) may be used to realize the benefits of the present invention.

Mechanical connectors such as RS-232 connectors (typically a "DB15" or "DB25") style connector, suffer from mechanical breakage and corrosion. The external contacts of the connector expose internal circuitry of the defibrillator 10 to potential damage from electrostatic discharge when connecting and disconnecting the patch cables. A further benefit of the infrared communications 220 over mechanical connectors and patch cables is the ability to electrically isolate the internal circuitry of the defibrillator 10, both from electrostatic discharge and also from ground loops that may introduce artifacts into the sensitive ECG measurement. Conversely, external communications circuits may be electrically isolated from the high voltages present in the defibrillator 10.

The defibrillator 10 is shown for purposes of example as a simplified block diagram that could be used to implement an AED. Additional functionality may readily be added that are typically found in the paramedic defibrillator 18 and the clinical defibrillator 22. For example, the ECG front end 202 could be modified to include capability for greater numbers of electrodes, such as three, five, and twelve lead monitoring electrodes for cardiac monitoring applications. Cardiac pacing functions could also be added. Other types of inputs for different types of devices, such as pulse oximetry sensors, may also be added for more advanced monitoring functions. The user interface 214 may also include additional components, including liquid crystal displays (LCDs), light emitting diodes (LEDs), buttons, softkeys, and switches well known in the art for user interface design to accommodate the more advanced functions. The printer 223 could be added to obtain print outs of the event summary 130 as needed.

During the treatment of the patient 14, the defibrillator 10 compiles the event summary 130. During the handoff from the first responder 12 to the ACLS provider 106, the event summary 130 is recalled from memory 218 by the controller 206 and sent to the infrared communications 220 for wireless information transfer to the paramedic defibrillator 108. In a similar manner, the event summary 130 contained in the paramedic defibrillator 108 may be sent via wireless information transfer to the clinical defibrillator 122 in the hospital emergency department 120. In this way, the event summary 130, either from the AED 104, the paramedic defibrillator 108, or both, finds its way to the attending physician alongside the patient 14 in order to obtain the most appropriate follow up treatment for the patient 14.

Figure 7:
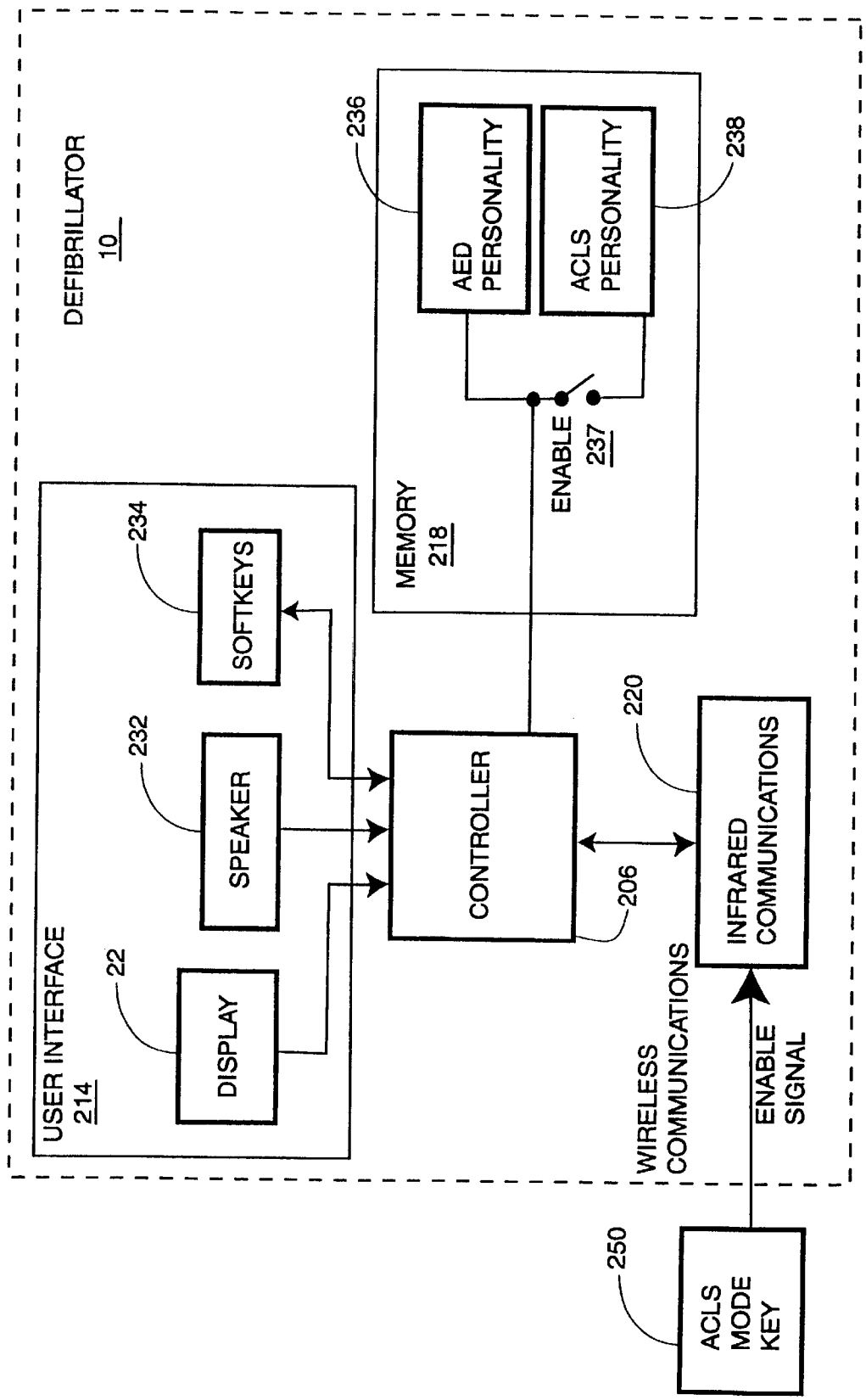
FIG. 7 is a simplified block diagram of the defibrillator of FIG. 2 showing an ACLS mode key which sends an enable signal via the wireless network.

FIG. 7 is a simplified block diagram of the defibrillator 10 illustrating the defibrillator 10 with access to an ACLS personality 238 controlled by an ACLS mode key 250 according to another embodiment of the present invention. The user interface 214 (shown in FIG. 5) includes the display 22, a speaker 232, and softkeys 234. The display 22 is preferably capable of displaying text and graphics. The softkeys 234 are mounted on the periphery of the display 22 such that text or graphics may be placed on the display 22 to operate as labels for the softkeys 234. Other types of displays as well as single function keys such as the shock button 24 may be readily substituted. The speaker 232 operates to provide audio such as voice prompts for the user.

Figure 8:
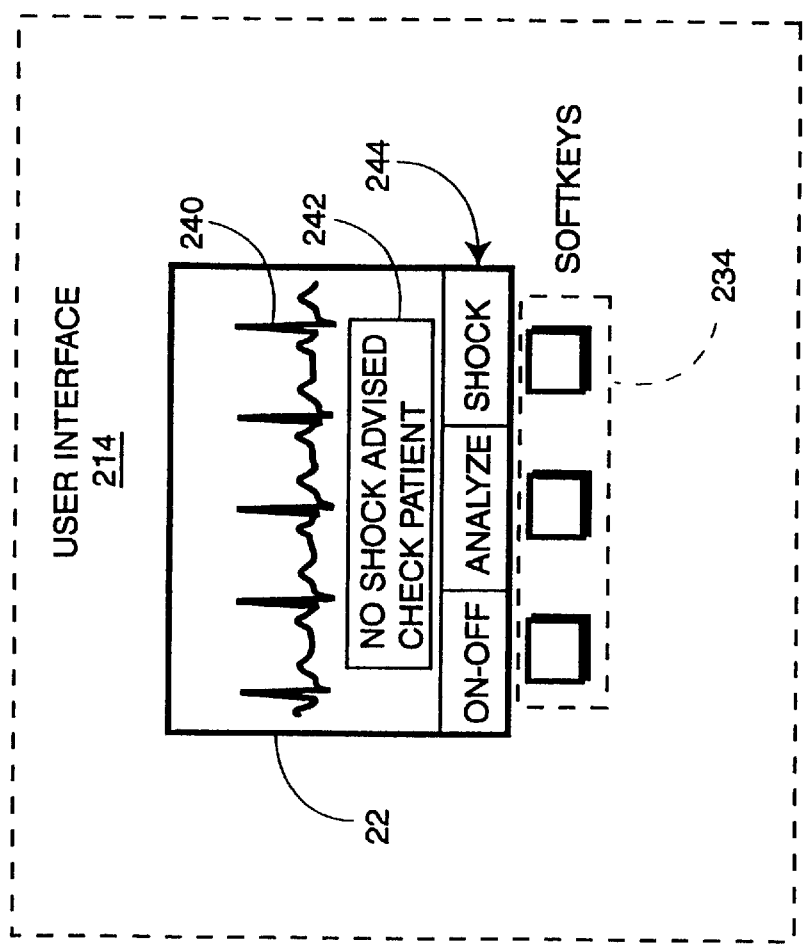
FIG. 8 is a diagram of a user interface of the defibrillator employing a graphical display device and associated softkeys with labels that can be changed depending on the selected personality.

A sample user interface illustrating the operation of the display 22 in conjunction with the softkeys 234 is shown in FIG. 8. The display 22 is capable of displaying graphics, such as an ECG trace 240, as well as text such as a message 242 labeled "NO SHOCK ADVISED CHECK PATIENT." The softkeys 234, shown as a set of three softkeys located adjacent to the display 22, have functions defined according to the particular personality selected for the defibrillator 10 which appear as a set of labels 244. The set of labels 244 shown could be used to implement an AED personality, with the softkey 234 labeled 'SHOCK" disabled until a shockable rhythm is detected. A voice message from the speaker 232 corresponding to the message 242 may also be used. As the hierarchy of functions determined according to the selected personality is navigated, the function of the softkeys 234 may be readily changed. The appearance of the display 22 can be readily changed for other operating modes.

Referring back to FIG. 7, the memory 218 contains at least two separate operating modes of the defibrillator 10 including an AED personality 236 and an ACLS personality 238. Each of these personalities defines a hierarchy of functions, displays, and menus that may be accessed by the user via the user interface 214. The paramedic defibrillator 108 and clinical defibrillator 122 would preferably have both the AED personality 236 and the manual personality 238 enabled for the ACLS provider 106 and hospital emergency department 120. The user interface 214 may be customized for each personality in terms of what appears on the display 22, what audio prompts are provided by the speaker 232 and what functions are mapped to the softkeys 234.

The AED personality 236 and ACLS personality 238 may be organized in such a way that the first responder 12 will see only AED functions defined according to the AED personality 236 on the user interface 214. The ACLS provider 106 may activate or enable the ACLS personality 238 through the use of an ACLS mode key 250. The ACLS mode key 250 may be any other peripheral capable of generating an enable signal that can be received by the infrared communications 220. The ACLS mode key 250 could be a dedicated unit with a single button similar to a remote control for consumer device such as a television or garage door opener. Alternatively, the ACLS mode key 250 could be implemented as a software program in a palmtop, laptop, or pen-based computer capable of infrared communications.

Upon receiving the enable signal from the ACLS mode key 250, the controller 206 operates to enable the ACLS personality 238 via an enable switch 237, allowing the ACLS provider 106 or hospital emergency department 120 access to advanced monitoring, defibrillation, or cardiac pacing functions. The enable switch 237 may be implemented in software simply as a flag or bit in the memory 218 that is set by the controller 206 to control access to the ACLS personality 238.

Conversely, the ACLS mode key 250 may send a disable signal to the defibrillator 10 to disable the ACLS personality 238 so that the defibrillator 10 operates only as an AED. In this way, the same defibrillator 10 may be used throughout an EMS system by personnel with different levels of training. For the first responder 12 such as a fire department, the defibrillator 10 is configured to operate as an AED 104. The same defibrillator 10 may later be issued to the ACLS provider 106 such as a paramedic unit with the ACLS personality 238 enabled using the ACLS mode key 250. Any number of such ACLS mode keys 250 may be issued to authorized personnel to obtain access to the ACLS personality 238 as needed. The enable signal required to enable the ACLS personality 238 may be readily changed, with the new enable signal given only to authorized personnel, to further prevent unauthorized access to the ACLS functions and simplify the administration of large numbers of the defibrillator 10 scattered throughout a large EMS system.

Figure 9:
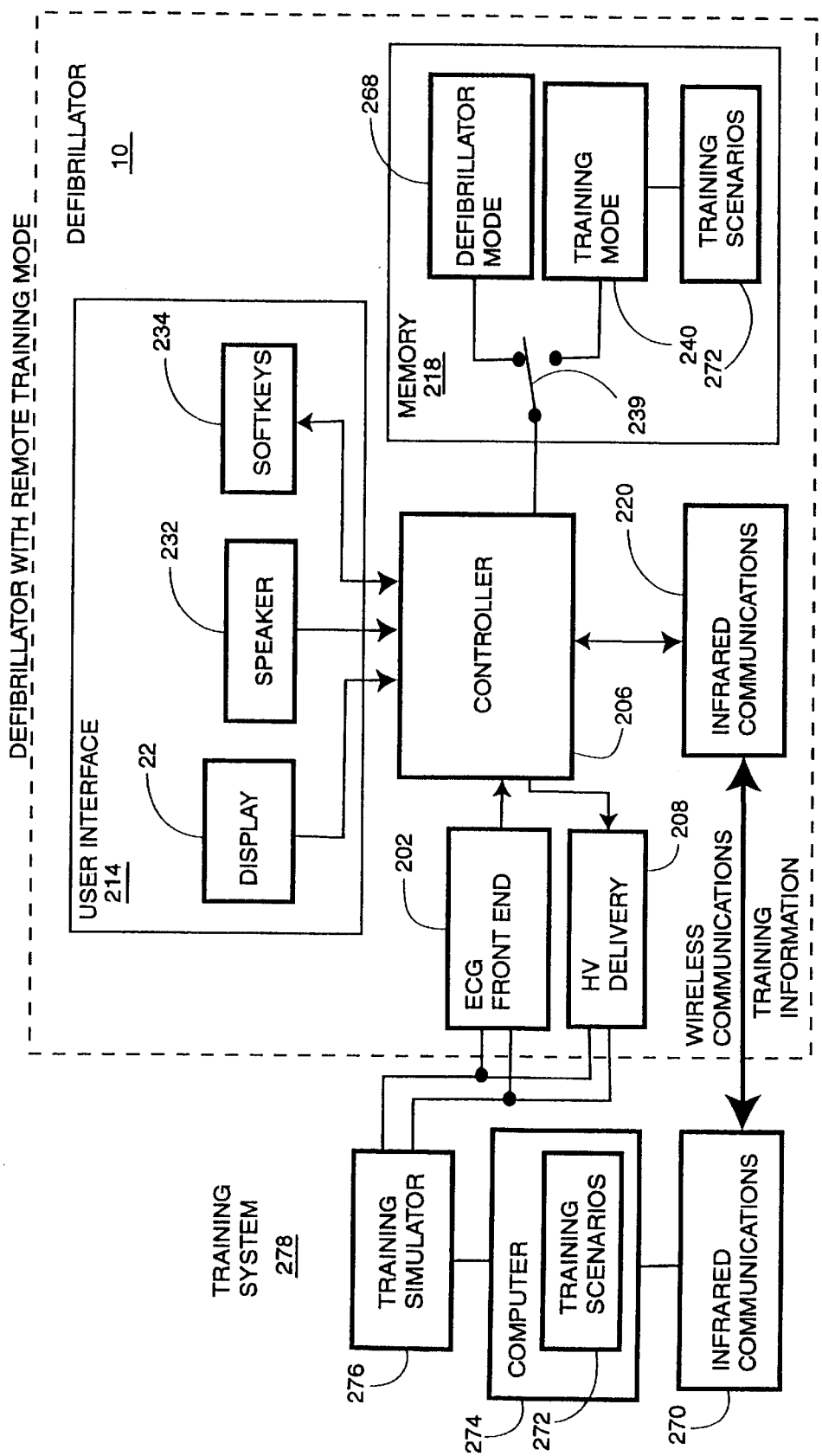
FIG. 9 is a simplified block diagram of the defibrillator of FIG. 2 showing a training system that is implemented via the wireless network.

FIG. 9 is a simplified block diagram of the defibrillator 10 illustrating the defibrillator 10 with access to a training system 278 via wireless communication according to another embodiment of the present invention. The training system 278 assists in training users to operate the defibrillator 10 using various training scenarios 272 contained in a computer 274. The computer 274 is connected to a training simulator 276 which may contain a test load for absorbing a defibrillation shock delivered by the defibrillator 10 and also a device for simulating selecting ECG patterns that may be analyzed either by the defibrillator 10 operating as an AED or by the user operating a paramedic defibrillator.

The training simulator is connected to the ECG front end 202 and to the HV delivery 208. For realistic training scenarios, it is desirable that the training simulator 276 take the form of a training mannequin in which the electrodes 16 must be applied in the correct places on the mannequin in order to properly deliver the defibrillator shock and receive the ECG signal. The training scenarios 272 may be downloaded to the defibrillator 10 via an infrared communications 270 connected to the computer 274 which communicates training information via wireless communications implemented with the infrared communications 220 or alternatively the RF communications 221. The training scenarios may then be stored in the memory 218. The training simulator 276 in the form of the training mannequin may also contain sensors to evaluate the efficacy of the CPR delivered by the trainee, including chest compressions and rescue breathing, similar to the Resusci Anne® mannequin produced by Laerdal Medical Corporation.

In a typical training scenario, the training simulator 276 would be configured to produce an ECG signal indicating VF. In such a scenario, the trainee arrives on the scene, evaluates the "victim" to find no pulse or breathing, and proceeds to start CPR while a partner deploys the defibrillator 10 and attaches the electrodes 16 to the training mannequin. The training system 278, which is running the selected training scenario 272, can download the training scenario 272 to the defibrillator 10 and upload results via the infrared communications 220. For example, the ECG signal acquired by the defibrillator 10 from the training simulator 276 can be uploaded via the wireless link to the computer 274 and compared against expected values to evaluate the placement of the electrodes 16. For safety reasons, the HV delivery 208 is preferably disabled while the defibrillator 10 is in the training mode 240. Eliminating the need to manually attach a communications cable or install a specialized training card in place of the memory 218 allows the training exercise to be more realistic and simpler to administer by training personnel.

As an example, the computer 274 could take the form of a palm top computer carried around between different training stations. In this way, the instructor could select from any number of training scenarios for a particular training station simply by walking over to that training station and pointing the infrared communications 270 at the defibrillator 10 to download the particular training scenario. Such flexibility in downloading training scenarios interactively selected by the instructor to the defibrillator 10 prevents students from "learning" a pre-programmed set of training scenarios in which the results become predictable.

As an alternative to connecting the defibrillator 10 to the training simulator 276, the user interface 214 can be programmed to simulate events such as the detection of VF according to the training scenario 272 without connecting the defibrillator 10 to a patient or the training simulator 276. In this stand-alone simulation mode, training requirements are simplified with reduced hardware requirements in the training system 278 because the training simulator 276 may be eliminated.

The results of the training exercise, which are similar to the event summary 130, can then be uploaded from the defibrillator 10 to the computer 274 and presented in the form of a report or incident summary. The wireless communication allows for a single computer 274 to readily communicate with multiple defibrillators 10, which is particularly desirable in a classroom environment with multiple training stations.

Figure 10:
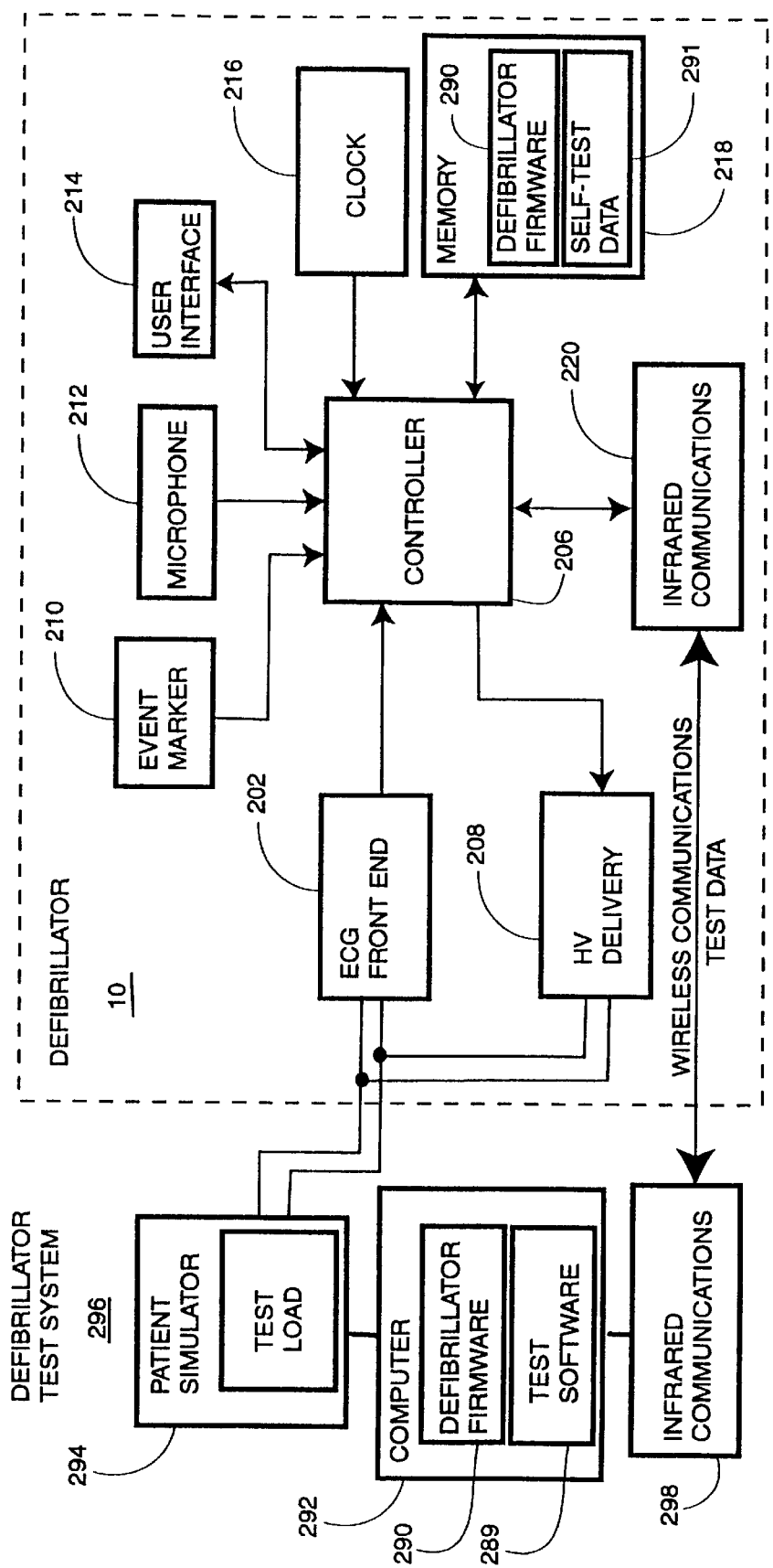
FIG. 10 is a simplified block diagram of the defibrillator of FIG. 2 showing a defibrillator test system that is implemented via the wireless network.

FIG. 10 is a simplified block diagram of the defibrillator 10 illustrating the defibrillator 10 with access to a defibrillator test system 296 via wireless communication according to another embodiment of the present invention. The defibrillator test system 296 may be used to test the defibrillator 10 during the manufacturing process as well as during service and maintenance of the defibrillator 10 over its service life.

A patient simulator 294 provides simulated ECG signals that are received by the ECG front end 202. The patient simulator 294 may also contain a calibrated test load (not shown) that receives and measures the defibrillation shock from the HV delivery 208 to provide measurement data about the defibrillation shock to ensure conformance to specification. A series of simulated ECG signals selected by a computer 292 may be generated by the patient simulator 294. The shock decisions generated by the defibrillator 10 may then be uploaded via the wireless network back to the computer 292 for comparison with expected results to ensure that the controller 206 properly distinguishes between shockable and non-shockable rhythms. Other parametric tests, including for example, sensitivity, common mode rejection, and noise figure of the ECG front end 202, may also be tested with the defibrillator test system 296 according to the present invention.

The computer 292 running test software 289 controls the patient simulator 294 to provide selected ECG signals and record the data from the defibrillation shock. Infrared communications 298 provides for coupling test data back and forth with the defibrillator 10 via wireless communications. The use of wireless communications allows for simpler testing of the defibrillator 10 with no concern with voltage isolation of the defibrillator test system 296 from data communication cables. The defibrillator 10 operates to analyze the simulated ECG signals and produce a shock decision.

A further component of the test may involve analyzing the shock delivered by the HV delivery 208 to a test load 295 in the patient simulator 294. The test load 295 may contain a range of impedances such as from 20 to 180 ohms to simulate the range of transthoracic patient impedances that may be encountered. Waveform parameters such as time and voltage characteristics may then be captured and recorded by the computer 292. The test data may also be down-loaded from the defibrillator test system 296 to the defibrillator 10 and stored in non-volatile portions of the memory 218 for record-keeping purposes. The shock delivery from the HV delivery 208 in the defibrillator 10 may be controlled via the infrared communications 220 according to the test software 289 to obtain shocks on request.

The computer 292 also contains defibrillator software 290 that may be a desired version of the firmware executed by the defibrillator 10 that needs to be downloaded via wireless communication. Such a down-load may be necessary to upgrade the firmware of the defibrillator 10 as is typically done over the life of a complex product to add enhancements or perform bug fixes. The down-load of the defibrillator software 290 may be accomplished via wireless communication for storage in the memory 218 without having to open the housing of the defibrillator 10 and physically replace read only memory (ROM) containing the firmware. In a manufacturing or depot test environment where many different models of defibrillators must be supported, standardizing on one type of wireless communication network such as the infrared IrDA protocol across all models and versions of defibrillators provides for substantially simpler support.

Because the defibrillator 10 is a complex instrument with many possible configurations of its AED personality 236 and ACLS personality 238, ensuring identical configurations among a population of defibrillators 10 is of great importance in an EMS system. Manually configuring each defibrillator 10 is time consuming and prone to error. The defibrillator test system 296 according to the present invention is capable of downloading the defibrillator firmware 290 that contains the desired configuration to multiple numbers of the defibrillator 10 to ensure identical configurations in each of the defibrillators 10 in the population. The download process may be done on an individual basis for each defibrillator 10 or simultaneously to as many defibrillators 10 as are in range of the wireless communication, either implemented with infrared communications 220 or RF communications 221.

In many applications, the defibrillator 10 is installed in a fixed location in a mounting bracket. The defibrillator test system 296, without the patient simulator 294, may be in the form of a laptop, palmtop, or pen-based computer that interrogates the defibrillator 10 via wireless communication to obtain internal self test data, current version of the defibrillator firmware 290, and battery condition as part of a regular maintenance operation. The infrared communications 220 may be implemented to provide wireless communication in such a way that the defibrillator 10 does not need to be removed from its mounting bracket or otherwise disturbed in order to communicate with the defibrillator test system 296 to obtain regular maintenance and service.

The defibrillator test system 296 may be used to particular advantage in obtaining device status and self test information from the defibrillator 10 without taking the defibrillator out of service. Periodically, the defibrillator 10, while in service, may perform self test operations to ensure that it is operational and ready for use. Self test data 291 collected during these self test operations may be stored in the memory 218 and uploaded via wireless communications to the computer 292 for storage and analysis.

Figure 11:
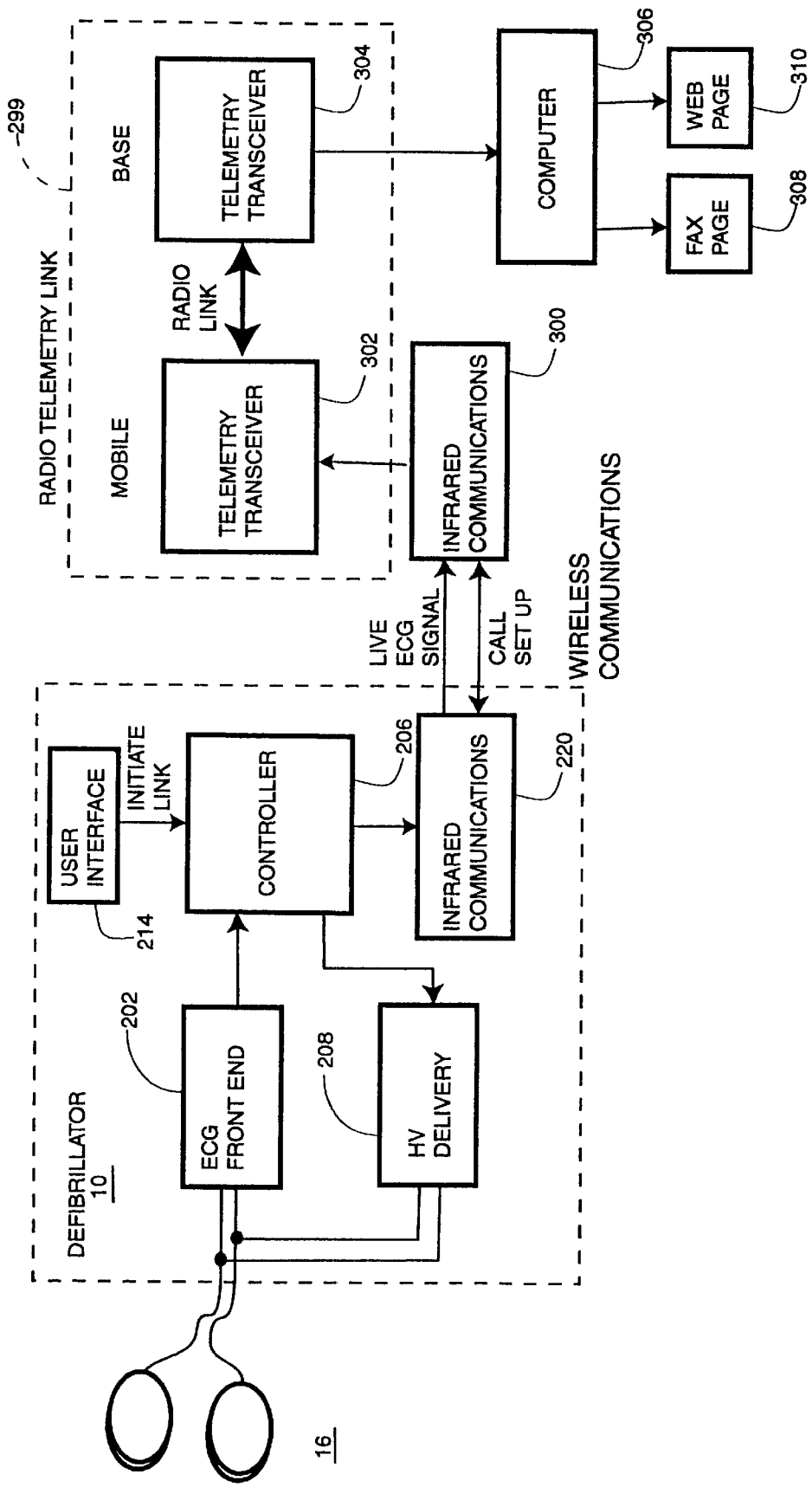
FIG. 11 is a simplified block diagram of the defibrillator of FIG. 2 showing the transmission of live ECG signals via a radio telemetry link.

FIG. 11 is a simplified block diagram of the defibrillator 10 illustrating the defibrillator 10 with wireless communication to a radio telemetry link 299 for transmitting a live ECG signal according to another embodiment of the present invention. A live ECG signal is the ECG signal collected from the patient 14 and transmitted to a remote location such as the hospital emergency department 120 where the ECG waveform may be displayed in real time to the attending physician.

The electrodes 16 are connected across the chest of the patient 14 as shown in FIG. 1 to acquire the live ECG signal from the patient 14's heart. The ECG front end 202 receives the live ECG signal and produces a stream of digital samples. The digital samples are sent to the controller 206 and passed along to the infrared communications 220 and further sent via wireless communication to an infrared communications 300.

Telemetry transceivers 302 and 304 communicate with each other via a radio link to form the radio telemetry link 299. Telemetry transceivers 302 and 304 can be implemented as conventional cellular telephones or cellular modems or via a dedicated radio link such as 800 MegaHertz (MHz) band radios. The infrared communications 300 is preferably built in as an integral part of the telemetry transceiver 302 in order to minimize the amount of cabling and separate boxes that must be kept track of. The telemetry transceiver 302 may be permanently mounted in the ambulance or aircraft avionics bay, for example, with no need to store an additional patch cable for connecting the telemetry transceiver 302 to the defibrillator 10.

The defibrillator 10 may then be used to configure the radio telemetry link 299 to provide a live ECG signal according the requirements of the local EMS without having to physically interface the defibrillator to the telemetry transceiver 302. Such ease of connection between the defibrillator 10 and telemetry transceiver 302 is particularly desirable in emergency situations where it is vital to rapidly communicate the live ECG signal to the physician with a minimum amount of set up time.

In response to an initiate link command generated by the user interface 214 to the controller 206, call set up information may be provided via the wireless communications to the radio telemetry link 299 which automatically initiates communications with the computer 306. The call set up information may include routing information such as telephone numbers, internet protocol (IP) addresses, universal resource locator (URL) internet address or other information necessary to set up the link to the computer 306 through a data communications network. Confirmation of a successful link set up using transport control protocols (such as TCP/IP) or similar network or link protocols may be returned to the defibrillator 10 via the radio telemetry link 299 which then begins sending the live ECG signal.

With the telemetry link now established, the computer 306 connected to the telemetry transceiver 304 receives the live ECG signal, now in the form of a stream of digital data or IP packets. The computer 306 processes the stream of digital data for display to the attending physician who may make the shock decision. The computer 306 may be configured to operate as a web server which receives the stream of digital data, formats the data according to a predetermined data structure, and then allows for viewing of the data using a web browser program on a web page 310. The use of web browser technology allows for multiple users and multiple computers to view the ECG data simultaneously while providing a common user interface. The computer 306 may also save the live ECG data for later viewing. Alternatively, the ECG signal may be formatted as a bit map image to form a fax page 308 which may be printed as a page on a fax machine or computer printer, or displayed on a computer monitor (not shown) connected to the computer 306. The fax page 308, in electronic form, may be updated rapidly to provide for the live ECG signal in close to real time fashion.

The wireless communication operates to provide access to the radio telemetry link 299 and has particular advantages in applications involving defibrillation in a confined environment such as in a building or on board an airliner. In the airliner scenario in which the patient 14 is a passenger, the defibrillator 10 is necessarily located in the passenger cabin with the patient 14 to provide emergency treatment. At the same time, the telemetry transceiver 302 needed to provide air-to-ground communications is likely integrated with the avionics equipment in the avionics bay of the aircraft. The infrared communications 300 may be permanently located in the passenger cabin to provide wireless communications between the defibrillator 10 and the telemetry transceiver 302 while eliminating problems associated with airborne electronics such as electromagnetic compatibility and high voltage isolation that commonly occur with communication cables.

It will be obvious to those having ordinary skill in the art that many changes may be made in the details of the above-described preferred embodiments of the invention without departing from the spirit of the invention in its broader aspects. Other types of wireless interfaces such as radio frequency modems that implement wireless local area networks, may be readily substituted for the infrared communications 220 as long as standardized communications protocols are substituted. Wireless modems available off the shelf that implement a standardized media access control (MAC) such as the Ethernet protocol could be readily implemented. Other medical equipment such as cardiac monitoring and diagnostic equipment would also benefit from the wireless communication described above.

Therefore, the scope of the present invention should be determined by the following claims.

What we claim as our invention is:

1. A defibrillator, comprising:
   a memory operable to store first and second defibrillator operating modes;
   an infrared communications circuit operable to receive an infrared mode-enable signal; and
   a controller coupled to the memory and to the infrared communications circuit, the controller operable to enable the first defibrillator operating mode in response to the infrared communications circuit receiving the mode-enable signal.

2. The defibrillator of claim 1 wherein:
   the first defibrillator operating mode comprises an advanced-cardiac-life-support mode; and
   the second defrbrillator operating mode comprises a basic-cardiac-life-support mode.

3. The defibrillator of claim 1 wherein the mode-enable signal conforms to an Infrared Data Association protocol.

4. The defibrillator of claim 1 wherein:
   the infrared communications circuit is operable to receive an infrared mode-disable signal; and
   the controller is operable to disable the first defibrillator operating mode in response to the infrared communications circuit receiving the mode-disable signal.

5. The defibrillator of claim 1 wherein the controller is operable to enable the second defibrillator operating mode regardless of whether the infrared communications circuit receives the mode-enable signal.

6. The defibrillator of claim 1, further comprising an infrared mode key operable to generate the infrared mode-enable signal.

7. The defibrillator of claim 1, further comprising a remote infrared mode key operable to generate the infrared mode-enable signal.

8. The defibrillator of claim 1, further comprising:
   an infrared mode key operable to generate the infrared mode-enable signal and an infrared mode-disable signal;
   wherein the infrared communications circuit is operable to receive the infrared mode-disable signal; and
   wherein the controller is operable to disable the first defibrillator operating mode in response to the infrared communications circuit receiving the mode-disable signal.

9. The defibrillator of claim 1, further comprising:
   a remote infrared mode key operable to generate the infrared mode-enable signal and an infrared mode-disable signal;
   wherein the infrared communications circuit is operable to receive the infrared mode-disable signal; and
   wherein the controller is operable to disable the first defibrillator operating mode in response to the infrared communications circuit receiving the mode-disable signal.

10. The defibrillator of claim 1, further comprising;
    an infrared mode key operable to generate the infrared mode-enable signal and an infrared mode-disable signal;
    wherein the infrared communications circuit is operable to receive the infrared mode-disable signal;
    wherein the first defibrillator operating mode comprises an advanced-cardiac-life-support mode; and wherein the controller is operable to disable the first difibrillator operating mode in response to the infrared communications circuit receiving the mode-disable signal.

11. A defibrillator, comprising:

a memory operable to store first and second defibrillator operating modes;

an infrared communications circuit operable to receive an infrared mode-disable signal; and a controller coupled to the memory and to the infrared communications circuit, the controller operable to disable the first defibrillator operating mode in response to the infrared communications circuit receiving the mode-disable signal.

12. The defibrillator of claim 11 wherein:

the first defibrillator operating mode comprises an advanced-cardiac-life-support mode; and the second defibrillator operating mode comprises a basic-cardiac-life-support mode.

13. The defibrillator of claim 11 wherein the controller is operable to implement the second defibrillator operating mode regardless of whether infrared communications circuit receives the mode-disable signal.

14. The defibrillator of claim 11, further comprising an infrared mode key operable to generate the infrared mode-disable signal.

15. The defibrillator of claim 11, further comprising a remote infrared mode key operable to generate the infrared mode-disable signal.

16. A method, comprising:

receiving an infrared mode-enable signal with a defibrillator that is operable in first and second operating modes; and enabling the first operating mode in response to the mode-enable signal.

17. The method of claim 16 wherein:

the first operating mode comprises a advanced-cardiac-life-support mode; and the second operating mode comprises a basic-cardiac-life-support mode.

18. The method of claim 16, further comprising generating the infrared mode-enable signal with an infrared mode key.

19. The method of claim 16, further comprising:

receiving an infrared mode-disable signal with the defibrillator; and disabling the first operating mode in response to the mode-disable signal.

20. The method of claim 16, further comprising:

generating the infrared mode-enable signal and an infrared mode-disable signal with an infrared mode key;

receiving the infrared mode-disable signal with the defibrillator;

disabling the first operating mode in response to the mode-disable signal; and wherein the first operating mode comprises an advanced-cardiac-life-support mode.

* * * * *